(12) United States Patent
Berci et al.

(10) Patent No.: US 8,702,602 B2
(45) Date of Patent: Apr. 22, 2014

(54) EXOSCOPE

(75) Inventors: George Berci, Los Angeles, CA (US); Benedikt Koehler, Emmingen-Liptingen (DE); Christoph Leidolt, Singen (DE); Frank Lederer, Tuttlingen (DE); Ulrich Weiger, Rangendingen (DE); Jan Dahmen, Seitingen-Oberflacht (DE); Fang Lei, Durchhausen (DE)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 13/436,231

(22) Filed: Mar. 30, 2012

(65) Prior Publication Data

US 2012/0265023 A1    Oct. 18, 2012

Related U.S. Application Data

(60) Provisional application No. 61/476,660, filed on Apr. 18, 2011.

(51) Int. Cl.
*A61B 1/06*    (2006.01)

(52) U.S. Cl.
USPC .................... 600/249; 600/101; 600/160

(58) Field of Classification Search
USPC ......................................... 600/101–183, 249
See application file for complete search history.

(56) References Cited

U.S. PATENT DOCUMENTS

| 4,727,416 | A | 2/1988 | Cooper et al. |
| 5,662,586 | A | 9/1997 | Monroe et al. |
| 5,908,294 | A | 6/1999 | Schick et al. |
| 6,554,765 | B1 * | 4/2003 | Yarush et al. ................ 600/132 |
| 2004/0077930 | A1 | 4/2004 | Guenier et al. |
| 2006/0281972 | A1 | 12/2006 | Pease et al. |
| 2009/0318758 | A1 | 12/2009 | Farr et al. |

FOREIGN PATENT DOCUMENTS

| WO | 2004100815 A2 | 11/2004 |
| WO | 2008153969 A1 | 12/2008 |

OTHER PUBLICATIONS

European Search Report Application No. EP 12 16 1540 Completed: Aug. 7, 2012; Mailing Date: Aug. 16, 2012 2 pages.

* cited by examiner

*Primary Examiner* — Mary Hoffman
*Assistant Examiner* — Christina Negrelli Rodriguez
(74) *Attorney, Agent, or Firm* — St. Onge Steward Johnston & Reens LLC

(57) ABSTRACT

An exoscope serves for observing and illuminating an object field on a patient from a position set apart from the patient's body. A lens system serves to observe the object field and an illumination serves to illuminate the object field. A distance between the lens system and the object field can be modified by a bracket. A shaft comprises on its distal end a head member that is widened in comparison to it, so that the illumination reaches into the distal-side head member. Positioned in the head member is at least one radiating illumination unit whose radiant characteristic can be adjusted in such a way that the object field can be illuminated homogeneously at all possible distances from the lens system. Supply lines for the at least one illuminating unit are positioned in the shaft.

19 Claims, 15 Drawing Sheets

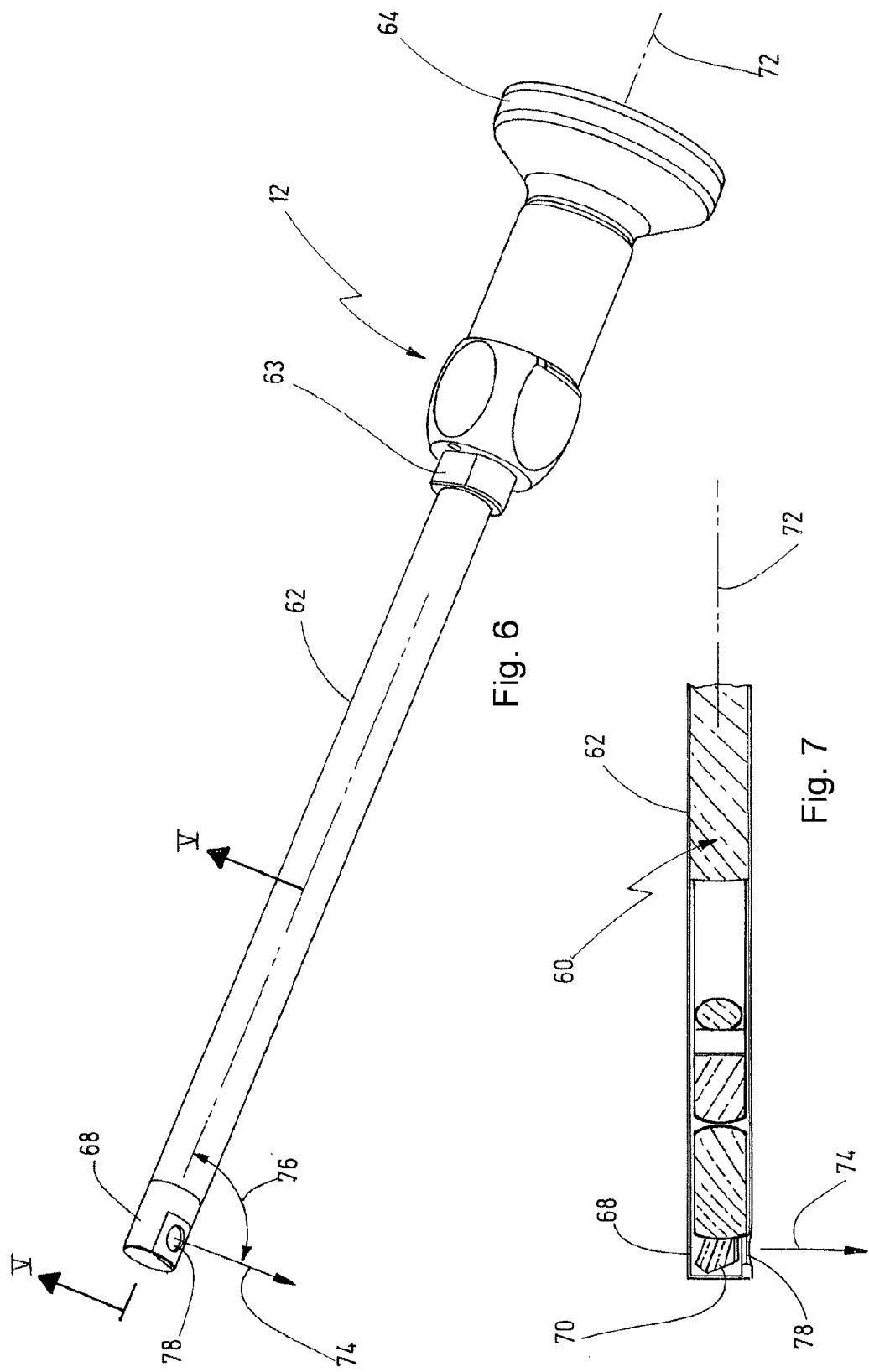

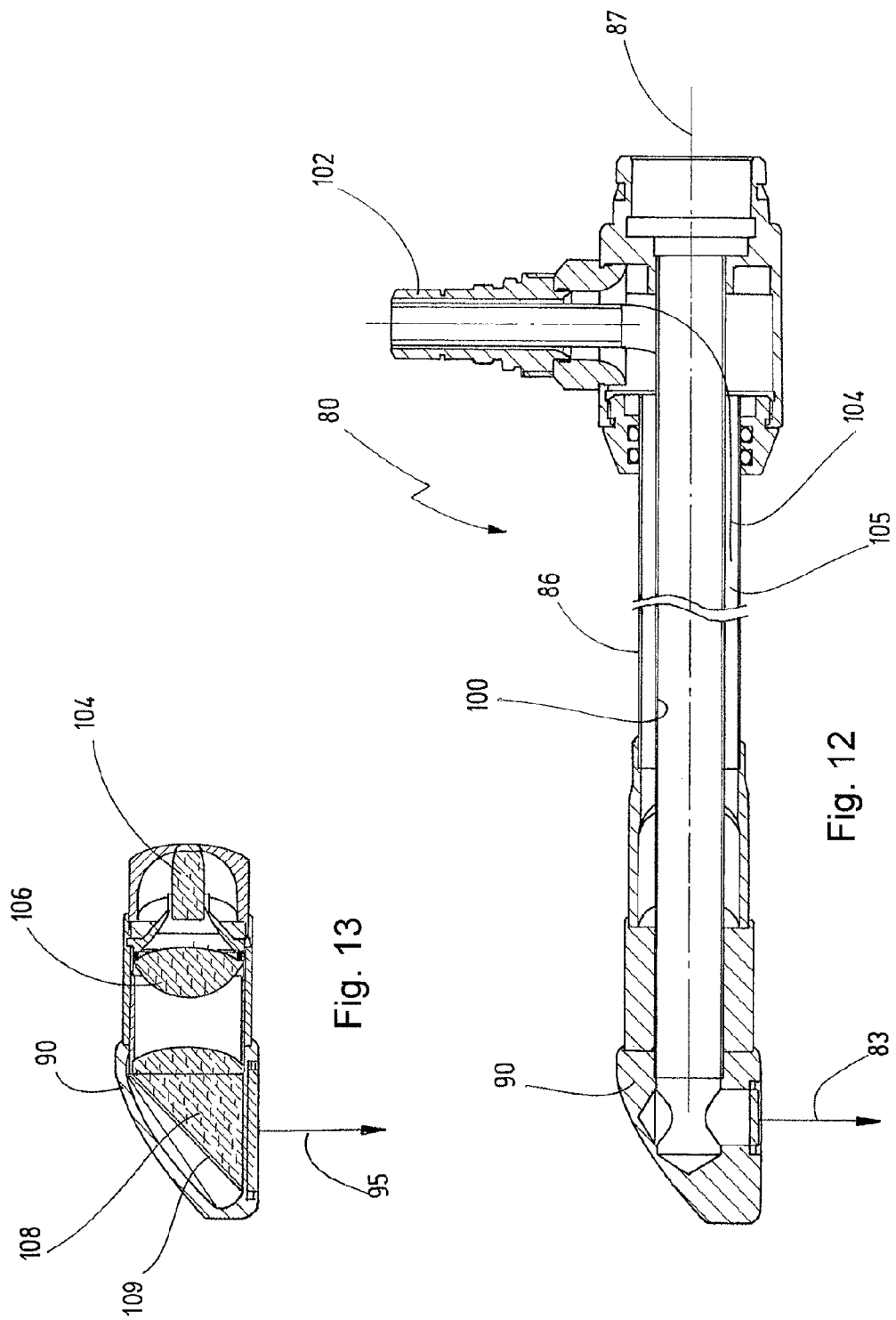

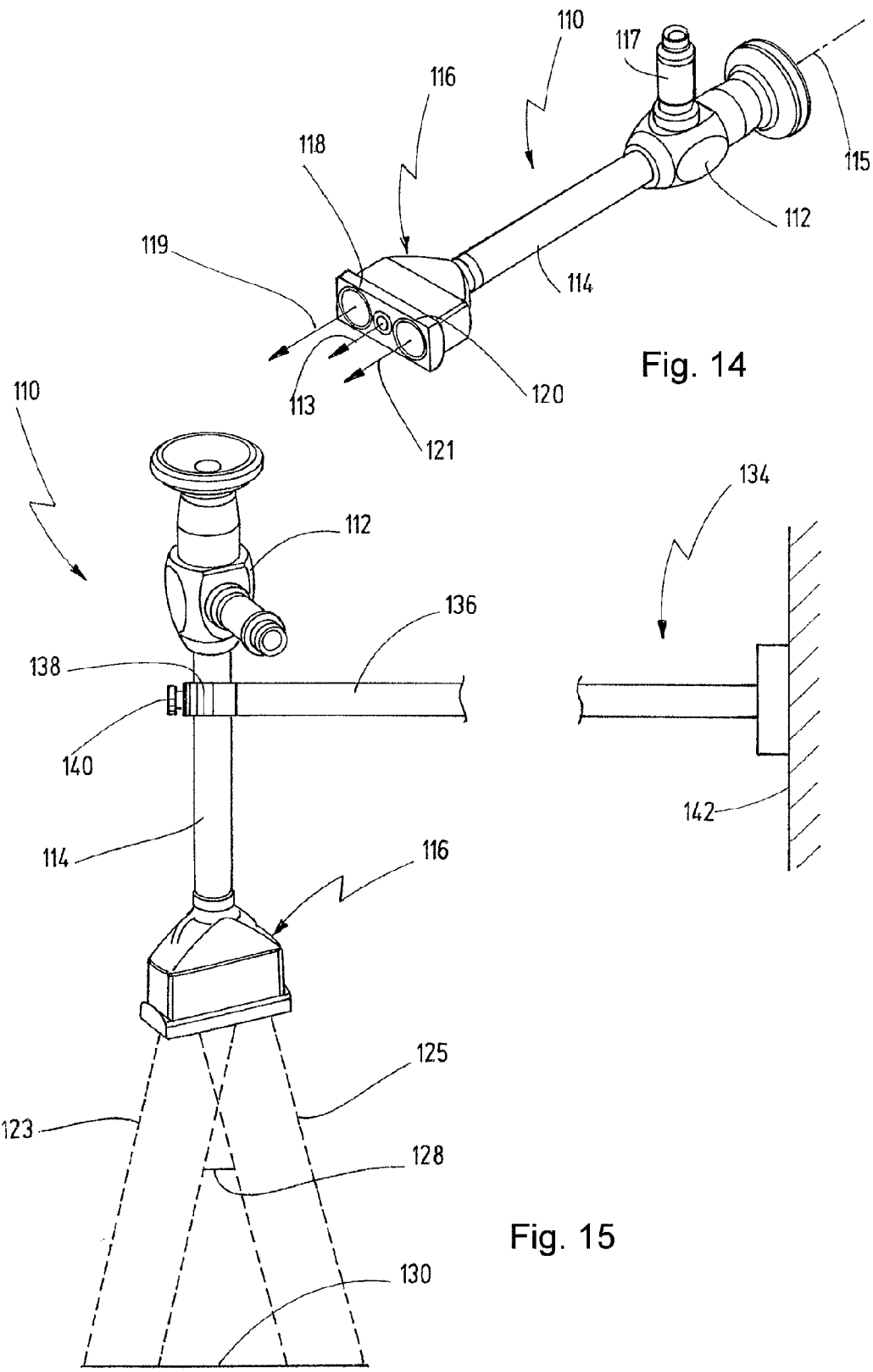

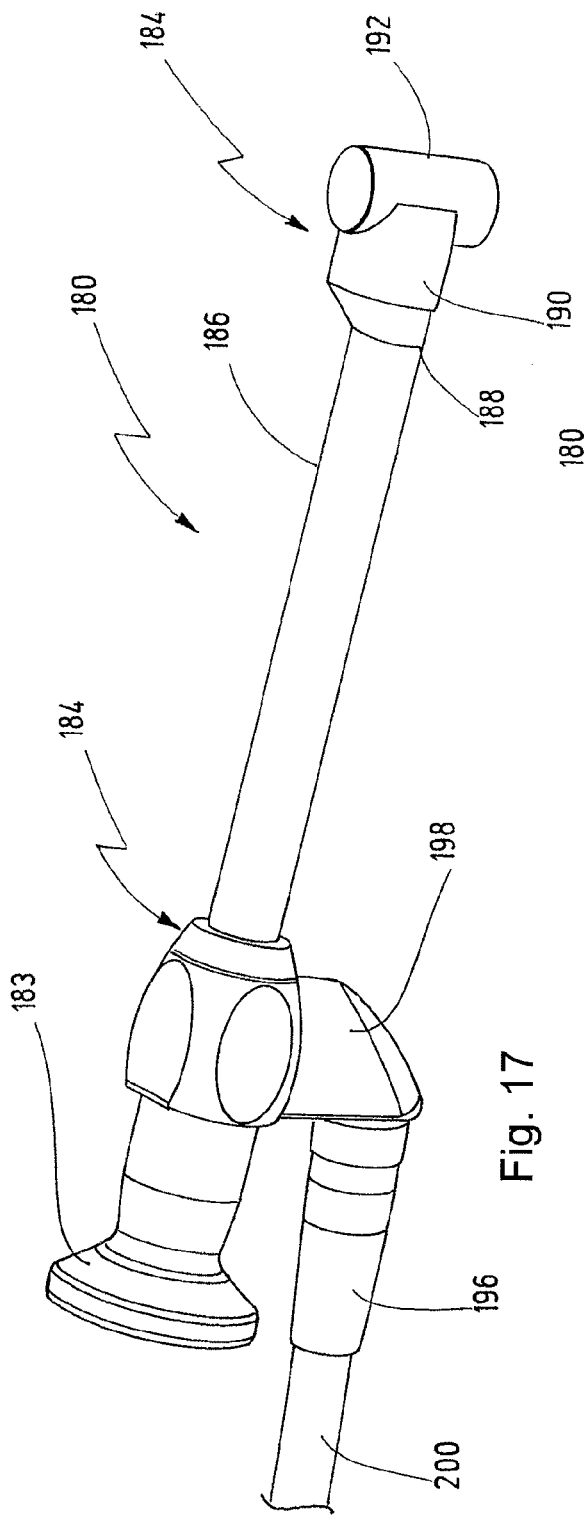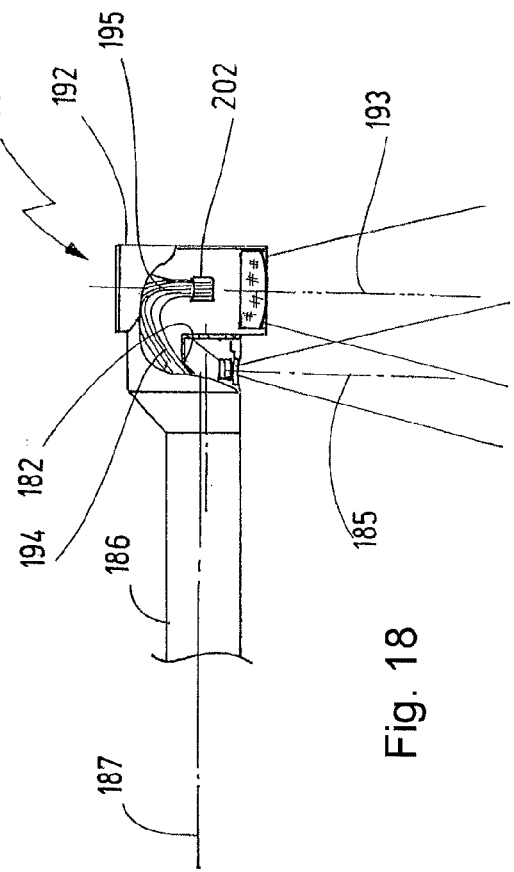
Fig. 17
Fig. 18

EXOSCOPE

CROSS-REFERENCE TO RELATED APPLICATIONS

The present application claims the benefit under 35 U.S.C. §119 (e) of the U.S. Provisional Patent Application Ser. No. 61/476,660 filed on Apr. 18, 2011.

FIELD OF THE INVENTION

The invention relates to an exoscope for observing and illuminating an object field on a patient from a site outside the patient's body, with a lens system for observing the object field and with an illumination to illuminate the object field, a distance between lens system and object field can be modified by a bracket.

BACKGROUND OF THE INVENTION

Apparatuses for illuminating an object field in an OR and also apparatuses for observing the object field are known in a variety of configurations.

From WO 2004/100815 A2, a surgical field illumination apparatus is known that comprises a large-surface illuminating unit and an integrated optic observation device. Here the observation device in particular can be a surgical microscope. This makes it possible to work with an optical observation device without requiring the presence of a tripod and a bracket for the optical observation device in addition to the tripod and bracket for the surgical field illumination. The apparatus is very unwieldy in structure and occupies a relatively large amount of space in the area above the object field.

Surgical microscopes for microsurgical disciplines are known under the designation M651 from the company Leica Microsystems AG, in Heer-brugg, Switzerland. These surgical microscopes are equipped with a built-in illumination by which the surgical site can be illuminated. This surgical microscope is also very unwieldy in structure, in particular because it comprises a very wide bracket in order to be able to bring the surgical microscope into numerous different positions relative to the object field. Surgical microscopes have a low depth of field, and thus in modifying the working distance it is often necessary to refocus.

Solutions have therefore been sought to provide apparatuses for observing and illuminating an object field that are less unwieldy and that in particular disturb the surgeon or possibly several persons participating in such an operation.

From WO 2008/153969 A1, an apparatus is known that is oriented to a configuration of an endoscope as is frequently used in minimally invasive surgery.

Endoscopes are thin elongated apparatuses with a relatively long, thin shaft. Integrated in the shaft is a lens system, in most cases a lens system made up of several long, thin rod lenses, a so-called HOPKINS rod lens system. Illumination consists in most cases of lighting lines fed in the shaft, said lines conducting light from a light conductor connection on the proximal side through the shaft as far as its proximal end.

The inner hollow spaces that are to be illuminated during minimally invasive surgery are relatively small, so that light of relatively low strengths is sufficient to illuminate such a surgical field, whether in laparoscopy inside an abdominal space or in arthroscopy in relatively small areas between joints.

The surgical site can be observed by the lens system. In visual observation, an eyepiece is provided on the proximal end of the shaft. The applicant itself in the past forty years has made a considerable contribution to further developing the technology of rigid endoscopes, with the result that the lens system makes possible a markedly sharp observation through such a shaft with the lens system mounted inside it.

In a refinement of this technology, a video camera was connected at the proximal end of the endoscope, said video camera recording the image and displaying it on a monitor. This led to a transformation of minimally invasive surgical technology in that surgeons are no longer required to keep their eye on the eyepiece during a procedure and thereby to observe the processes carried out inside the body but instead observe this on a monitor. In difficult operations and especially those that last for some time, it becomes less tiring for the surgeon to observe an image on a monitor rather than constantly gazing through an endoscope with one eye.

This technology requires intensive training on the part of the surgeon, because he is observing in fact the processes he himself performs inside a body, not through an endoscope positioned directly in front of him but rather via a monitor positioned outside and laterally removed from the surgical site. This requires a relatively lengthy practice phase, but then leads to the surgeon being able to perform minimally invasive procedures in a relatively relaxed position, whether standing or seated. This applies likewise to supporting staff or assistants who are now not required to observe the surgical site through additional trocars placed in the body with lens systems inserted through them, but who instead can now observe this on one and the same monitor.

This technology now makes it possible to visually record and store the entire operation procedure. The digitally stored image, at the same time, can also be exchanged with other hospitals, and in fact this is also possible live during a procedure. Consequently, specialists can be actively involved in an operation, directly viewing the image captured by the video camera so that they then can lend support to the surgeon.

In the aforementioned WO 2008/153969 A1, an attempt was made to create apparatuses for extracorporeal visualization in medicine on the basis of this type of endoscope.

This apparatus is mounted by means of a bracket in such a way that, through the lens system, an object field can be observed at a distance of a few centimeters, such as in the range of 20 cm, from the distal light outlet or image entry end. The optical properties were adjusted accordingly for this working distance. The term "exoscope" is derived from this fact; that is, meaning an observation instrument based closely on successful invasive endoscope technology but serving for extracorporeal illumination and observation of an object field.

It was observed in practical use that endoscopes of this type, for reasons inherent to the system, were subject to certain restrictions. If the distances between the lens and the object field are relatively large, such as more than the previously mentioned 20 cm, the object field can no longer be sufficiently observed and the lens no longer conveys an optimal image.

If one assumes, for example, an open heart operation in the chest area, then the sternum must first be sawed along its entire length and spread wide apart by means of so-called rib retractors. Only then is there any access at all to the inner sternum area and/or the still beating heart. These rib retractors are mechanically very stable tools, which are relatively unwieldy and accordingly demand a sufficiently large space for manipulation over the object field. This requires a certain minimum distance from the observation lens.

In an actual open-heart surgery intervention, after the preparation, that is, once the sternum has been sawed open, the sternum spread apart, and the heart exposed, relatively large areas are observed and illuminated. At the end of such an operation, for example after replacement of coronary vessels, very minute manipulations must be performed and relatively small areas must be observed and illuminated, for example if vessel implants must be sewed and affixed to the heart wall on existing vessels. The observation lens is required to provide an optimal image in each case in all surgical steps.

SUMMARY OF THE INVENTION

It is therefore the object of the present invention to further develop an exoscope for the purpose of providing a stable, robust structure and ensuring that an object field can be sufficiently illuminated and observed at distances that extend to the meter range.

This object is achieved according to the invention by means of an exoscope that comprises a shaft on whose distal end a head member is positioned that is wider than the diameter of the shaft, the illumination reaches into the distal side of the head member and it is possible to position in the head member at least one radiating illuminating unit whose radiant characteristic can be selected in that the object field can be homogeneously illuminated at all possible distances from the lens and wherein power lines are positioned in the shaft for the at least one illuminating unit.

These measures have numerous advantages for the use of an exoscope. Providing a head part that is wider than a shaft makes it possible to configure the shaft in all cases as a relatively thin structure and thus not cumbersome or of wide configuration. By providing a head member that is wider than the shaft, it becomes possible to integrate a sufficiently powerful illumination therein, which can also homogeneously illuminate surgical sites in great distances up to a meter. The head member is markedly larger and in particular wider than the shaft, in particular by a multiple.

A radiation direction occurring under an angle from the longitudinal axis of the shaft opens to mount the exoscope in an inclined or horizontal extension to an object filed. This advantageously provides more space at the object field for the surgeon to operate and use instruments without impacting a vertically positioned exoscope.

In one embodiment, the depth of the head member is about the same as the diameter of the shaft. This provides more space around the head area of the exoscope for the surgeons to operate.

Additionally, guiding the light conductors within the shaft avoids unnecessary junctions for connecting with light connectors of other parts. This results in a marked reduction in light loss in the areas of such junctions. This allows for most of the light to effectively be used to illuminate the operation site.

Because the power lines for illumination are integrated in the shaft, there are no exposed power lines running from the distal to the proximal end that would not only require additional structural space but also would include the risk that staff might become entangled therein. Because the head member is enlarged in comparison with the shaft, it is possible to integrate or position therein one or more radiating illuminating units, so that a radiant characteristic can be selected that allows homogeneous illumination over the entire range of variable distances.

This has the advantageous consequence that the head member can be positioned at a relatively small distance of just a few centimeters from the object field and in addition that the object field can thereby be optimally illuminated, in particular homogeneously, and this is also possible even when the head member is at a considerable distance, such as a meter, away, requiring working distances preferably of 20 to 60 cm. Accordingly powerful illuminating units must be provided that also generate the corresponding heat, and thus the head member must make it possible to integrate such components, to convey them and to incorporate them in good working order.

The head member also allows other components to be integrated such as filters, diaphragms or the like, to make it possible to conduct medical procedures such as photodynamic therapy, photodynamic diagnosis, autofluorescent methods or ICG (indocyanine green) examination. The optical system itself is designed to provide an optimal image at all times over the entire variable working distance, whereby the working distance can vary from about 20 cm to about 1 m, preferably up to 60 cm. The lens system, depending on its design, can be integrated into the shaft, but in such case the distal end of the lens system likewise is positioned in the head. This makes possible varying positions of the radiating illumination units relative to the distal end of the lens system.

When there is only one illuminating unit, the distal end of the lens system can be positioned in the axial direction of the shaft upstream or downstream from the illuminating unit, or these components can also be positioned beside one another.

Assuming a configuration with two illuminating units, they can be positioned on both sides of the distal end of the lens system; with more than two radiating illuminating units, they can be positioned around the distal end of the lens system. This depends on the purpose for which the exoscope is being used, that is, whether it is intended to illuminate relatively small or large object fields. Depending on the configuration of the illuminating units, necessary power lines can be fed through the shaft to the head member. If illuminating light is generated directly in the head member, for example by light diodes, the electric lines can be fed through the shaft. If the light is fed through light conductors, they can be placed in the shaft.

In another configuration of the invention, the radiating illuminating units are equipped with focusing that comprises condenser lenses.

This feature has the advantage that the head member also integrates a focusing device whereby optimal focusing of the illuminating light can be achieved for the particular object field. In this case each illuminating unit can comprise its own focusing device, and with several illuminating units, all of them or groups of them can be equipped with a common focusing device. The radiant characteristic or homogeneous illuminating depth can be pre-selected as a default setting by the manufacturer.

In another configuration of the invention the light beams, which can be emitted by the several radiating illuminating units, can be adjusted in such a way that the light beams overlap so that the surgical site can be illuminated homogeneously by the overlap area.

Not only does this contribute to an optimal illumination of the surgical site or object field, but also the control and operation are relatively simple. Corresponding adjustment devices, for example focusing devices or the like, can be mounted in or on the head member because a sufficiently stable base is present in the exoscope to incorporate such additional components and also to operate them. Consequently, optimal illumination is achieved at varying working distances, in particular in the preferred range of 20 to 60 cm.

In another configuration of the invention the illuminating units comprise distal ends of light conductors, which are fed from a proximal light conductor connection via the shaft into the head member.

This feature has the advantage that the actual light source can be positioned off to the side of the exoscope, and thus the surgical area is not encumbered and the light can be directed by the light conductors to the particular illuminating unit.

In another configuration of the invention the light conductors are fed in the shaft as a skein and include strands in the head member that lead to the particular radiating illuminating unit.

This feature has the advantage that the shaft makes possible a relatively slender structure, and separation or fanning into various strands is possible in the enlarged head member.

In an additional configuration of the invention a viewing angle of the lens system and a radiating direction of the illuminating unit occur in the direction of a longitudinal axis of the shaft.

This feature has the advantage that the exoscope can be set up to stand above a surgical site, and when the OR is suitably configured the bracket can be configured so that the exoscope can be positioned suspended from a ceiling. This arrangement is especially favorable during an actual intervention when it is not absolutely necessary to work intensively in this direction, that is a direction standing perpendicular above the surgical site. If a video camera is connected on the proximal end of the lens system, it makes sense to select the working distance in such a way that a person standing at the operating table can operate the camera.

In another configuration of the invention, the viewing angle of the lens system and a radiating direction of the illuminating units are at an angle to the longitudinal axis of the shaft.

The advantage of this feature is that with an exoscope in a stationary position for example, lateral areas of a body can be illuminated, for example during hip surgery with a patient lying on the back. Another advantage of this configuration consists in now positioning the shaft itself at an incline and to leave both the viewing direction of the lens system and the radiating direction of the illuminating device u unchanged in vertical direction. This configuration is used when wide-ranging manipulations are required across the surgical area. With a viewing angle of the lens system that is not equal to zero degrees, the shaft, video camera, light conductors, cables, and so on are no longer directed toward the surgeon but instead can run laterally. As a result, the surgeon is less restricted in his freedom of movement and has a freer view.

In an especially advantageous configuration of the invention, the angle is approximately 90 degrees.

In the 90 degree configuration the exoscope or the shaft can be directed to point approximately horizontally away from the object field and never-theless the object field can be illuminated and observed from above, that is in vertical direction. If a video camera is connected to the lens system, its operating elements are positioned at a height that is favorable for operating staff, so that it can be controlled in ergonomic manner.

In another configuration of the invention the radiating direction is diverted through at last one prism or mirror inserted in the head member.

This feature has the advantage that the prism or mirror provided for the diversion can be positioned directly in the head member. As a result, the illuminating light can be directed for example through the straight shaft into the head member and then diverted there through correspondingly configured prisms.

In another configuration of the invention the radiating direction is diverted through corresponding curvature of the distal end areas of flexible light conductors.

The advantage of this feature is that the flexibility of light conductors, for example those made of glass fibers, can be exploited to achieve the corresponding diversion of the illuminating light away from the longitudinal axis of the shaft in simple manner. Here again, the configuration of the head member as wider than the shaft is favorable, because in this wider head member these curved segments can be incorporated so as to be protected from outside.

In another configuration of the invention the lens system is configured as a separate component that can be inserted into the head member.

This feature has the notable advantage that the illuminating part of the exoscope and the lens system are configured as two different components that can be combined to form the complete exoscope. It is known in the endoscope art how to configure such lenses as autoclavable, and therefore one can have direct access here to a wealth of experience with this technology. Not only does this configuration simplify the installation, disassembly, and cleaning of the exoscope, but it also opens up numerous possible variations. Thus, the illuminating part of the exoscope can be configured as a kind of base member into which various lenses with different optical properties can be inserted. Examples of these optically diverse properties can be different depths of field or different enlargements of the lens systems. It is also possible of course to configure the illuminating part with corresponding variety and to connect it with standard lens systems. Such a configuration will be useful when illuminating systems of varying power are desired but when basically unchanged optical properties are desired or sufficient for the lens system.

This markedly increases the range of application of such an exoscope.

This modular construction makes it possible to provide correspondingly suitable combinations of illuminating parts and lens parts for a particular operation, even in the preparatory stage in assembling the surgical instruments.

In another configuration of the invention a guide device is present on the shaft through which the lens system can be connected to the head member.

This feature has the advantage that in modular construction the lens system can be directed to the head member through the guide device with accuracy and seated precisely.

In another configuration of the invention a base member is present that can be coupled with the lens system.

The advantage of this feature is that the base member can be called on during use independently of the lens system.

The lens system can thus be mounted in a position that is most favorable for observation.

Then the base member with the illuminating units can be installed off to the side, that is, apart from the lens system in a position that is especially favorable for the illumination. These parts can of course be combined and also used together. Flexibility is increased precisely by the fact that these module parts can be separated from one another and can be positioned in the surgical field correspondingly separate from one another.

In another configuration of the invention the base member is composed of modules that already comprise at least an illuminating unit and its power lines.

The advantage of this feature is that here the flexibility is increased still further. Each module part comprises a shaft and at least one illuminating unit. Thus it is possible to position several such module parts with one or more illuminating units at various points in the surgical field, depending on the which of these arrangements is most favorable for an optimal illumination.

These parts too can of course be combined and, as mentioned before, can be used in combination. They can also be stored and kept ready in this condition, and only when the particular application requires it can the module parts be used singly or combined in groups, depending on what is best suited to the field of application. If one location in the surgical area must receive especially intensive illumination during a procedure, then one module part with one or more illuminating units can be removed from the exoscope assembly and be specifically conveyed either by hand or by a bracket to this site that is to be illuminated. When no longer needed, it can be combined again with the other components.

In another configuration of the invention, every module comprises a shaft and a head member, which can be affixed to one another by a separable fastening.

Advantageous in this feature is the fact that every module part has the characteristic of the exoscope, that is, the slender shaft and widened head member, and that, by means of a fastening, all modules as well as the lens system can be used either together or partly joined together.

This increases the flexible uses of such an exoscope.

In another configuration of the invention the head member is configured as a closed housing, which is connected with the shaft on the proximal side.

This feature has the advantage that this sealing prevents penetration of contaminants into the interior of the head member. Thanks to a corresponding hermetic sealing, the head member can likewise be autoclavable, whether as a modular individual part or in assembled state or firmly positioned with a lens system.

In another configuration of the invention the lens system comprises a video camera that is coupled to it and that is connected with a monitor to display the images from the video camera.

The advantage of these features is that the observation technique that is familiar from minimally invasive surgery in connection with endoscopes and has by now become established, can also be used directly on an exoscope. Video cameras in the meantime can be produced in extremely small sizes and with relatively light weight, so that coupling a video camera to the proximal end of the exoscope is simple and can be accomplished without disturbing stability or operating security. This position also lies, in most cases, relatively apart from the surgical area, and thus because of the video camera and its required power lines and cables, no adverse effects occur. Familiar standard connections can be used here in order to couple the video camera to the eyepiece.

The video camera can perform an enlargement in simple manner, namely by the zoom. Complex optical components, in addition, are required for surgical microscopes and can make the device cumbersome and expensive.

In another configuration of the invention the lens system comprises an eyepiece enlargement by which a full-surface image can be achieved on the monitor at all zoom settings of the video camera.

In the predominantly round optical instruments a circular-shaped diaphragm is present. Projected onto a rectangular monitor, parts of the monitor remain black in the corner areas. To make full use of the monitor for the video image, in particular at 16:9 formats, the zoom characteristic is adjusted so that a diaphragm is not visible even at 1× zoom.

It is understood that the characteristics cited heretofore and those that are yet to be described can be applied not just in the indicated combinations but also in other combinations or independently, without departing from the framework of the present invention.

The invention is hereinafter described in greater detail with reference to a few embodiments in connection with the appended drawings, which are as follows.

BRIEF DESCRIPTION OF THE DRAWINGS

FIG. 6 shows a perspective view of the lens removed from the base member of FIG. 5;

FIG. 7 shows a longitudinal section along the line V-V in FIG. 6;

FIG. 12 shows a section along the line X-X in FIG. 11;

FIG. 13 shows a section along the line XI-XI in FIG. 11;

FIG. 14 shows a perspective view of a third embodiment of an exoscope facing straight ahead;

FIG. 15 shows, strongly schematized, a possible arrangement of the exoscope of FIG. 13 held in vertical alignment by a bracket;

FIG. 17 shows a fifth embodiment of an exoscope with only one illuminating unit and 90 degree view;

FIG. 18 shows a longitudinal section in the area of the head member of FIG. 17;

DETAILED DESCRIPTION OF THE INVENTION

Figure 1:
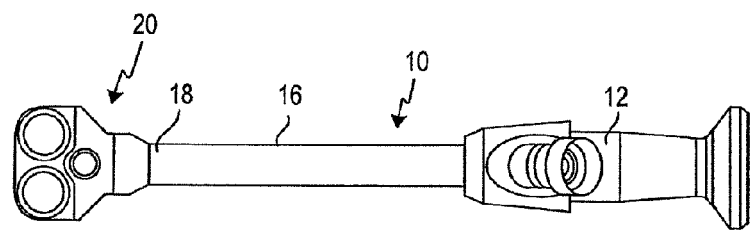
FIG. 1 shows a bottom view of one advantageous embodiment of the exoscope.

Referring now to the drawings, wherein like reference numerals designate corresponding structure throughout the views.

Figure 2:
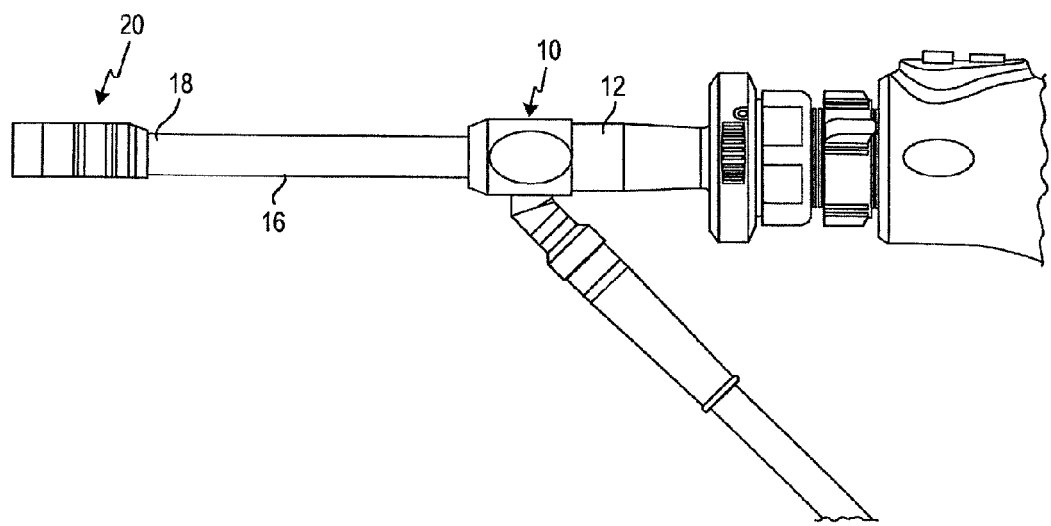
FIG. 2 shows a side view of the advantageous embodiment of FIG. 1.

An embodiment of the exoscope 10 is illustrated in FIGS. 1 and 2. Another embodiment of the exoscope 10 is shown in FIGS. 3-8. It should be understood that the structure and function of the exoscope 10 in FIGS. 1 and 2 is similar to that illustrated in FIGS. 3-8. Accordingly, the two embodiments will be described together with the differences between the embodiments specifically discussed.

The exoscope 10 comprises a lens system 12. The lens system of the embodiment of FIGS. 1 and 2 has the lens system mounted fixedly. The lens system of the embodiment of FIGS. 3-8 is configured as a modular, self-contained component.

One notable difference from the embodiment in FIGS. 1 and 2 and that of FIGS. 3-8 is the low profile head member 20.

FIGS. 1 and 2 illustrate a head member 20 that has a depth that is almost equal the diameter of the shaft 16, which can be seen in FIG. 2.

Figure 3:
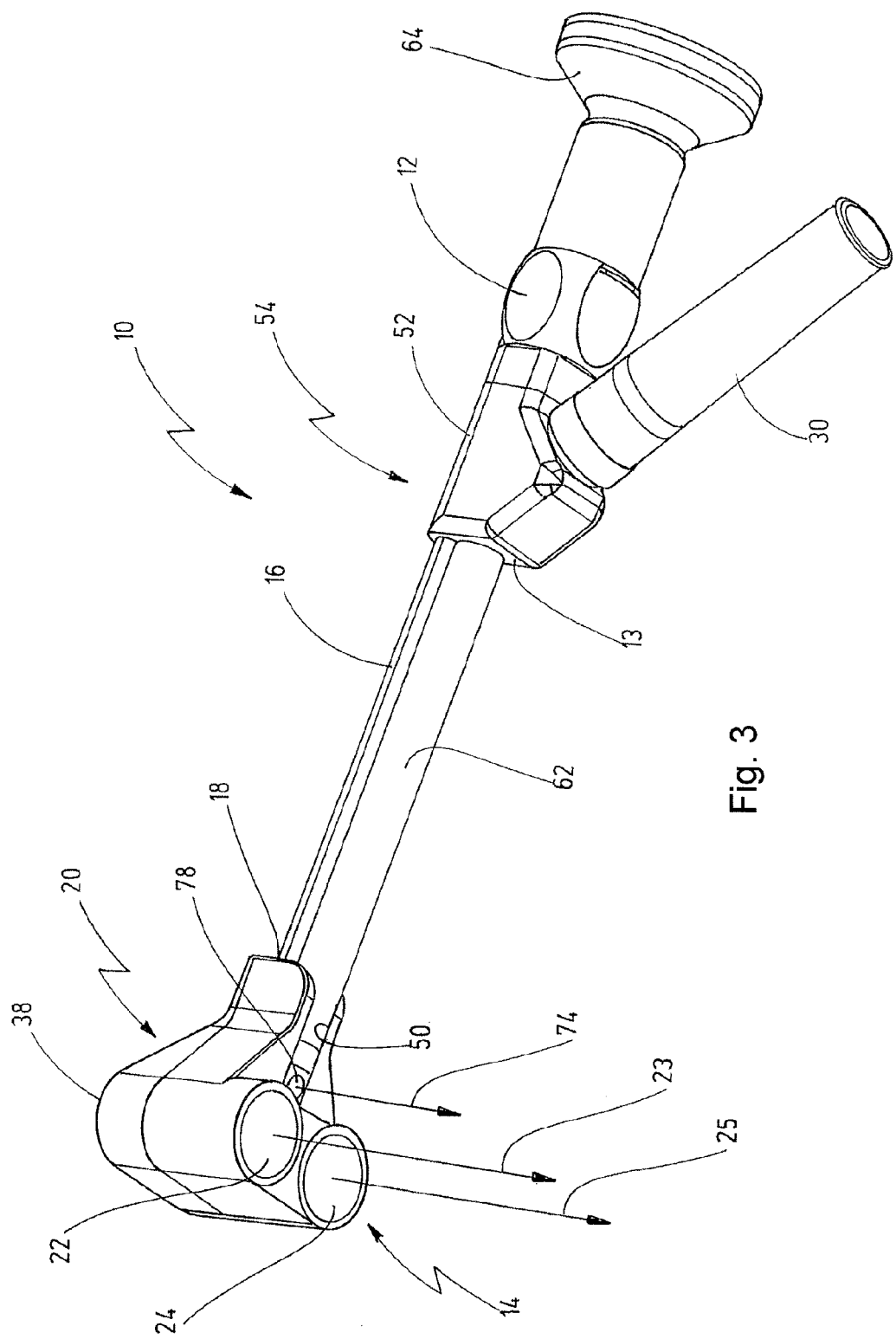
FIG. 3 shows a perspective view of an embodiment of an exoscope from diagonally below, that is, approximately contrary to the radiation or viewing direction of the lens system.
Figure 4:
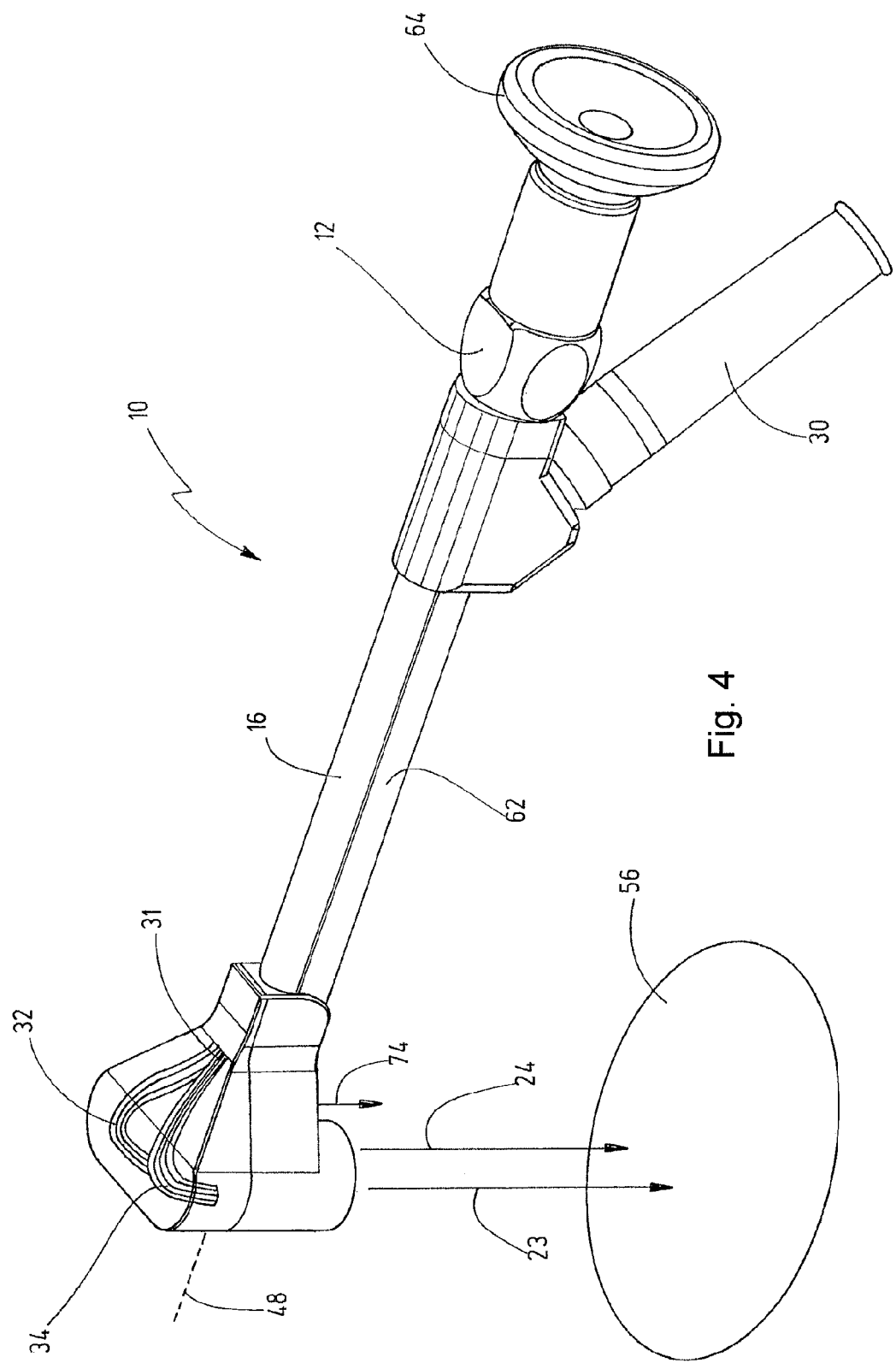
FIG. 4 shows corresponding perspective view from above.

Another difference from the embodiment shown in FIGS. 3-8 is that, the skein 31 of the light conductors in FIGS. 1 and 2 does not have bended branches as shown in FIG. 4 at 32 and 34. Rather, the light guides in the embodiment of FIGS. 1 and 2 extend straight into the head member 20 and light is directed about 90 degrees via a prism integrated into the head member 20 (see FIG. 13 in particular for the construction of the integral prism).

One of the advantages of the low profile head embodiment is that the head member 20 is very thin and the fiber bundle is guided within the shaft 16 to the head member 20. The chances of the fiber bundles becoming damaged is therefore reduced.

In addition, the exoscope 10 comprises a base member 13, in which the illumination 14 is integrated. The base member 13 comprises an elongated, approximately half-bowl-shaped rigid shaft 16 whose distal end 18 is connected with a head member 20.

Integrated in the head member 20 is a first illuminating unit 22, which emits light in a radiating direction 23. In addition, a second illuminating unit 24 is also positioned in the head member 20 and likewise emits light in a radiating direction 25. As can be seen in particular from the sectional view of FIG. 8, supply lines 26 are positioned inside the base member 13 to convey illuminating light to the illumination units 22 and 24. Provided for this purpose is a light conductor connection 30, which is positioned laterally from the proximal end of the shaft 16 and in which a skein 31 of light conductors 28 is inserted. The skein 31 is composed of a bundle of numerous flexible glass fibers, known per se from the field of endoscope construction. This skein 31 is fed in the shaft 16 as far as the head member 20, where it is separated, as can be seen in particular from FIG. 4, into two branches 32 and 34, which lead respectively to the illuminating units 22 and 24. Situated on the underside, that is, on the radiating side of the head member 20, is a corresponding radiation opening 36, which is hermetically sealed off by an optically active window 40.

The head member 20 comprises a housing 38 that is closed on all sides and firmly connected with the rigid shaft 16.

Figure 8:
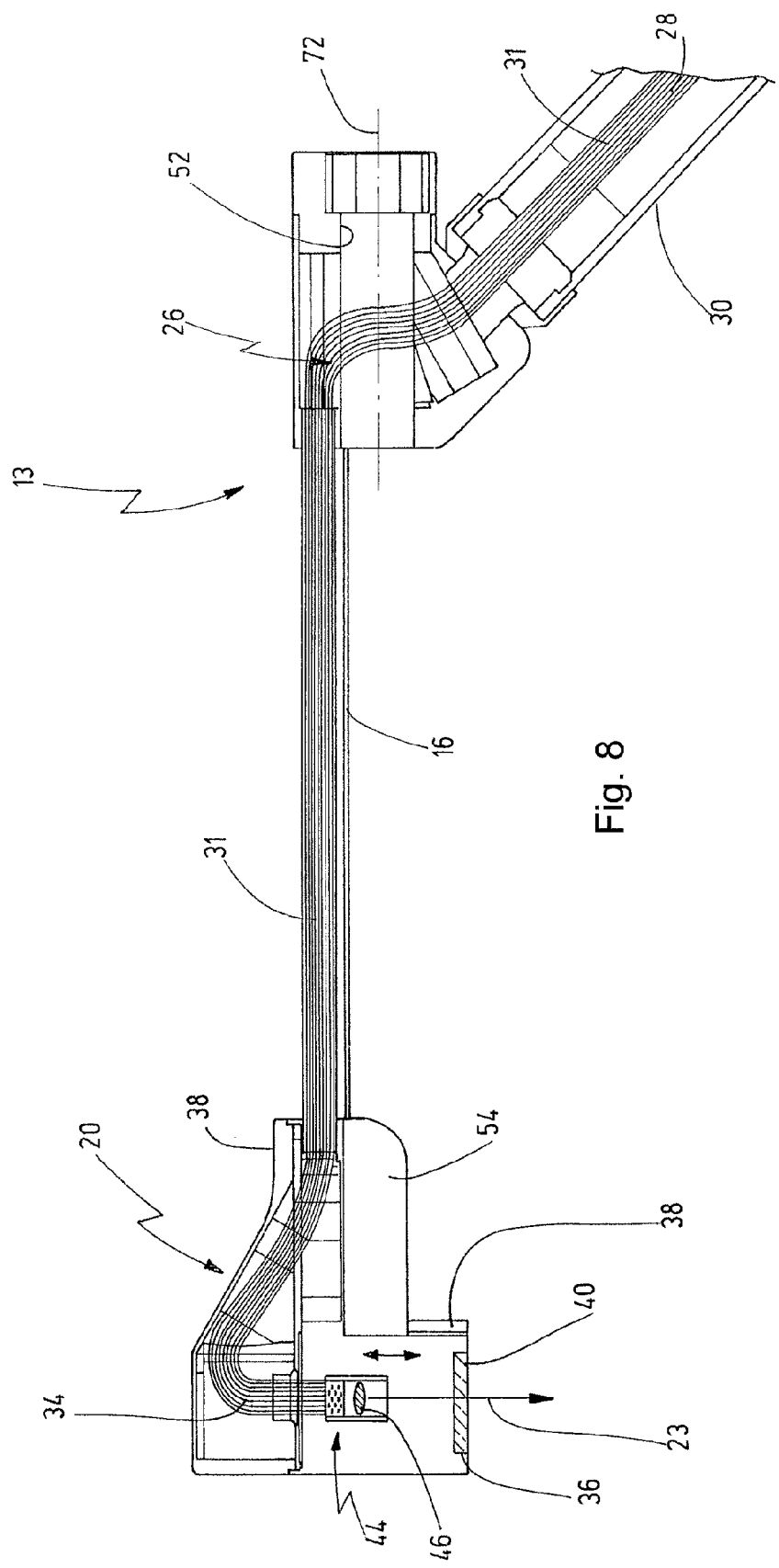
FIG. 8 shows a strongly schematized longitudinal section through the base member as seen in FIG. 5, that is, without the lens system inserted and in particular to show the guidance of the light conductors.

As can be seen in particular from FIG. 8, a focusing device 44, integrated in the head member 20, comprises slidable condenser lenses 46 in order to achieve a focusing of the illuminating light.

The housing 38 is as a rule sealed for insulation and thus autoclavable. The condenser lens 46 also ensures that the individual light conductors are not configured but rather that the illumination field is homogeneous. The producer in most cases already provides the settings, which the user cannot modify. However, should a movement of the condenser lenses be desired, integrated positioning organs can also be installed in the head member 20, for example positioning rings or positioning discs that can be operated from outside and whose rotation produces a back-and-forth sliding of the condenser lenses 46 in the illuminating direction 23.

Figure 5:
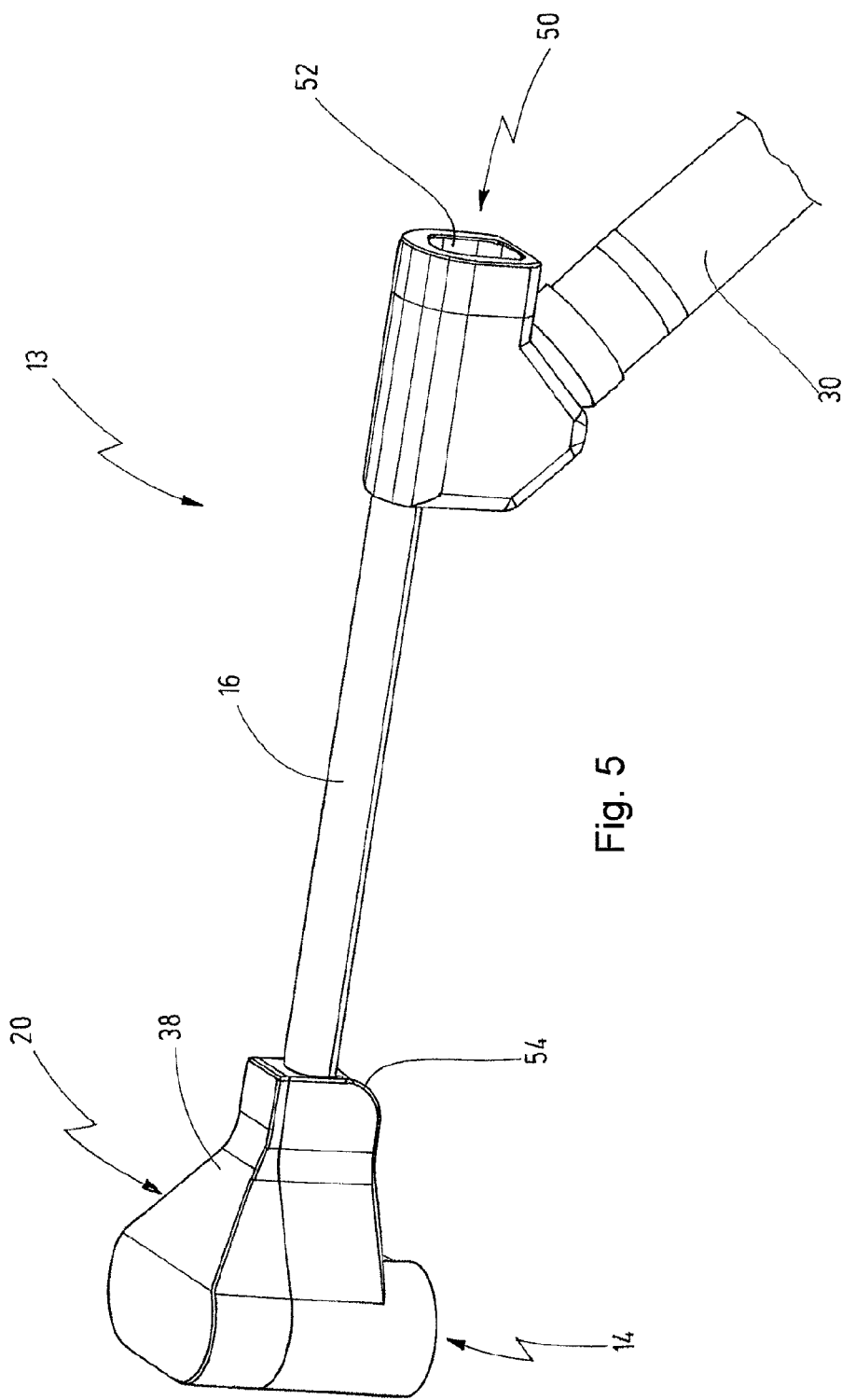
FIG. 5 shows a perspective view of the base member of the exoscope with the lens removed.

It can be seen from the drawings in FIGS. 3 through 5 that the radiating directions 23 and 25 of the illuminating units 22 and 24 run diverted at an angle of about 90 degrees from the longitudinal axis 48 of the shaft 16.

It can be recognized in particular from FIGS. 3 and 5 that a guide device 50 for the lens system 12 is provided on the base member 13. The guide device 30 comprises on the proximal end of the shaft 16 a hollow guide sheath 52, from which the lateral light conductor connection 30 also extends outward.

The proximal end of the head member 20 is configured as a type of duct 54 into which the distal end section of the lens system 12 can be inserted.

During assembly, the lens system 12, as seen in FIG. 6, is advanced from the distal to proximal side through the housing 52 along the shaft 16 in distal direction until the distal end portion is inserted into the duct 54 as seen in FIG. 3. A coupling site 63 on the lens system 12 ensures a particular rotation direction for the lens system 12 with respect to the base member 13.

The lens system 12 itself, as can be seen in particular from FIGS. 6 and 7, comprises an elongated lens shaft 62 on whose proximal end an eye-piece 64 is screw-mounted.

Enclosed within the lens shaft 62 is a lens system 66, for example a rod lens system known from the endoscope construction art according to HOPKINS. Positioned on the distal end 68 of the lens system 66 is a prism 70 that ensures that a viewing direction 74 results, at an angle 76 of approximately 90 degrees from the longitudinal axis 72 of the lens shaft 62. A corresponding transparent window 78 closes off the lens shaft 62 laterally in this area of the viewing direction 74. The prism 70 can be assembled of several prisms.

As can be seen in particular from the perspective view in FIG. 3, the window 78 then is at such a position that the viewing direction 74 is approximately aligned with and parallel to the radiating directions 23 and 25 of the illuminating units 22 and 24.

This configuration of the exoscope 10 with a 90 degree angle and 90 degree illuminating direction with respect to the longitudinal axis of the shaft 16 is applied when, as shown in FIG. 4, an object field 56 is to be illuminated and observed in which the exoscope 10 is intended not to take up too great an area of the object field 56. The exoscope 10 is held and directed by a bracket, not presented in any greater detail here, in such a way that it extends diagonally to the surface of the object field 56 away from the surgical site.

A second embodiment of an exoscope, shown in FIGS. 9 through 12, is designated in its entirety with reference number 80. Here too the exoscope 80 comprises a lens 82 and an illumination 84. Here as well, an elongated cylindrical shaft 86, closed and hollow in this embodiment, is foreseen with a head member 90 mounted on its distal end 88. A first illuminating unit 92 as well as a second illuminating unit 94 is also positioned in the head member 90. Here, again, the radiating direction 93 of the illuminating unit 92 as well as the radiating direction 95 of the illuminating unit 94 is directed in such a way that it runs at an angle of approximately 90 degrees to the longitudinal axis 87 of the shaft 86.

The lens 82 is inserted from the proximal end into a guide tube 100 of the shaft 86 and is firmly connected with the head 90, as can be seen in FIG. 12.

Figure 9:
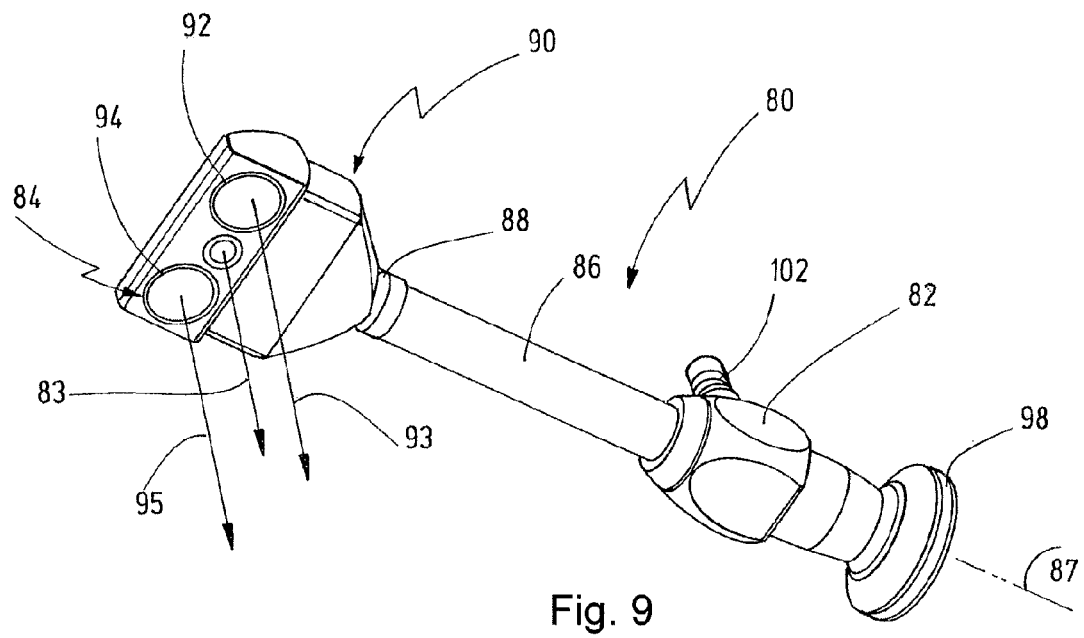
FIG. 9 shows a perspective view comparable with that of FIG. 3 of a second embodiment of an exoscope.
Figure 10:
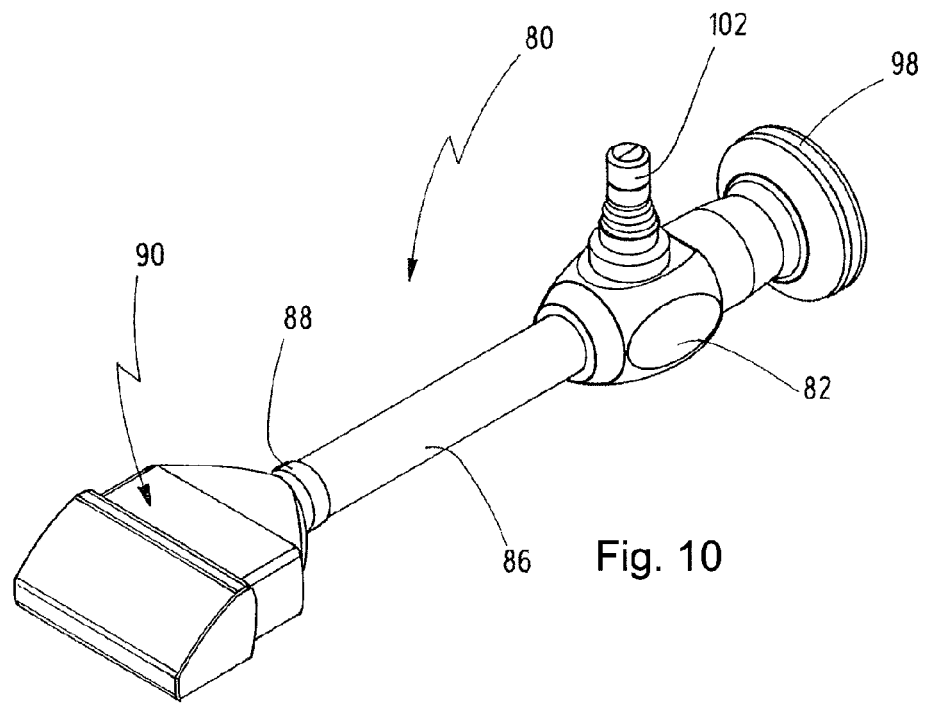
FIG. 10 shows a perspective overhead view of the exoscope of FIG. 9.
Figure 11:
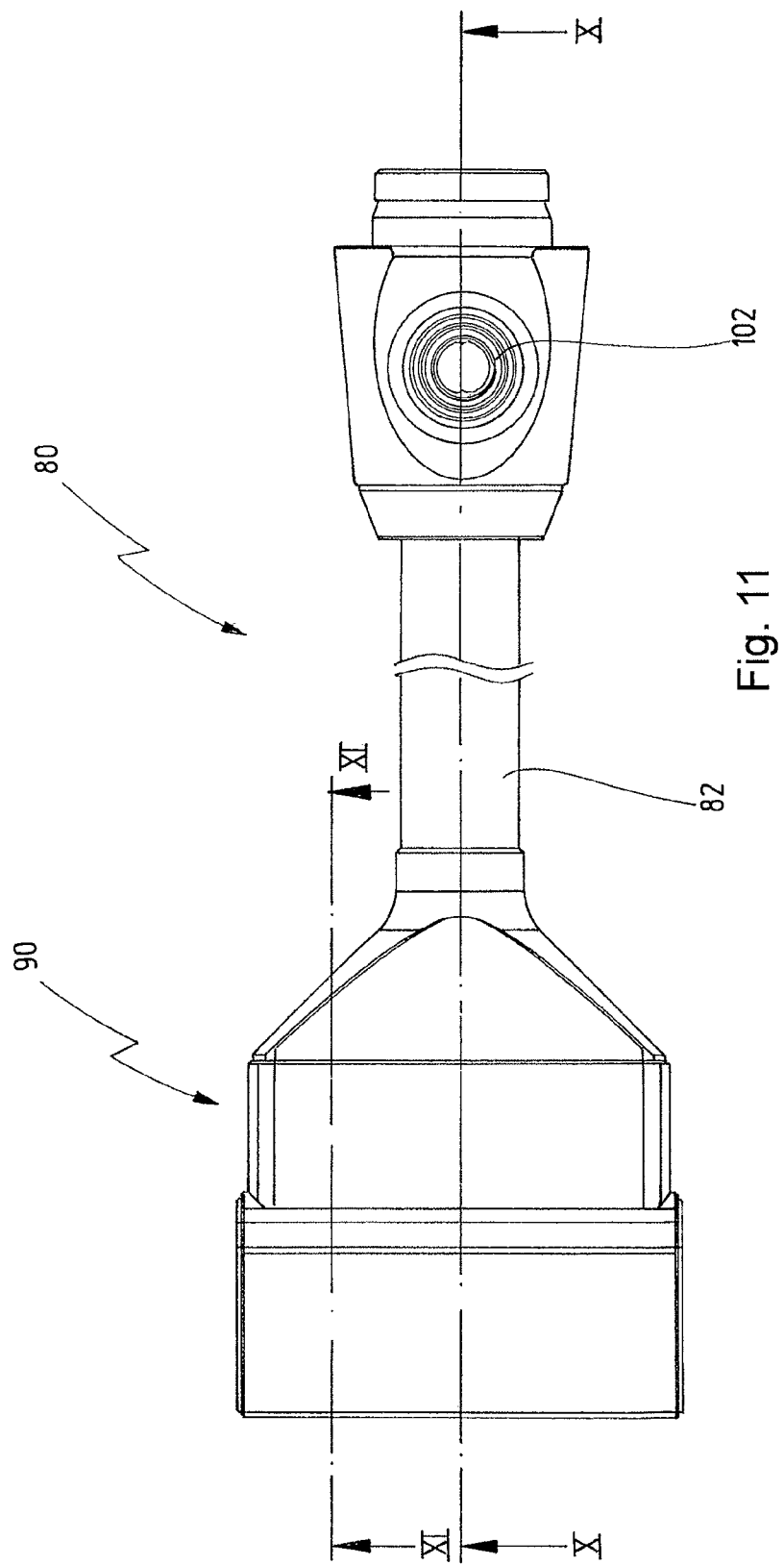
FIG. 11 shows an overhead view of the exoscope of FIG. 9.

The lens 82 too is once again configured as a 90 degree lens, that is, its viewing direction 83, as can be seen in particular from FIG. 9, runs at a 90 degree angle to the longitudinal axis 87 of the shaft 86, in which the shaft of the lens 82, not presented in greater detail here, is inserted. Here too the arrangement is such that the lateral window, by which the 90 degree view is made possible, is positioned in the head member 90 and also positioned, as can be seen in particular from FIG. 9, between the two illuminating units 92 and 94. The lens 82 is equipped with an eyepiece 98.

A light conductor connection 102 protruding laterally from the proximal end of the shaft 86 serves, again, to contain light conductors 104, which, as visible in the sectional drawing of FIG. 12, are positioned in an intermediate space 105 between the outer shaft 86 and the guide tube 100 and are fed in distal direction to the illuminating units 92 and 94.

It can be seen from the sectional drawing in FIG. 13 that a prism 108 is positioned in the head member 90 and diverts illuminating light fed by the light conductors 104 at a 90 degree angle from the longitudinal axis 87 into the radiation direction 95. A lens inserted in between ensures that this illuminating light diversion occurs with as little divergence loss as possible. Instead of the prism 108 a mirror 109 can be used for diverting the illuminating light.

It can be seen in particular from the perspective drawing in FIG. 9 that the two illuminating units 92 and 94 and the inlet of the lens 82 positioned between them are positioned in the viewing direction 83 in a row that runs diagonally to the longitudinal axis of the shaft 87.

It is also possible to direct this row in such a way that it runs in the direction of the longitudinal axis 87. Here the row can lie directly in the direction of the longitudinal axis 87, or it can be displaced laterally to left or right so that with certain operating techniques, if desired, working space is made available immediately beside the head member 90 on one side of the longitudinal axis 87. It is not essential here that these three structural elements lie on a straight line but they can instead lie on a curved line. In the embodiments in which more than two illuminating units 92 and 94 are foreseen, for example with three or four, they can be positioned accordingly around the distal end of the lens 82.

Illustrated in FIGS. 14 and 15 is a third embodiment of an exoscope, which is designated in its entirety with the reference number 110. The exoscope 110 also comprises a lens 112 that is enclosed in a shat 114. The viewing direction 113 of the lens 112 here follows the direction of the longitudinal axis 115 of the shaft, and is thus a lens 112 with a zero degree viewing angle. Here too, once again, positioned on the proximal end of the shaft 114 is a head member 116 in which two illuminating units 118 and 120 are enclosed whose radiating directions 119 and 121 are likewise aligned in the direction of the longitudinal axis 115. FIG. 15 shows how the exoscope 110 is mounted on a stationary site 142 by means of a bracket 134. This site is usually the operating table or a special tripod.

For this purpose the bracket 134 can comprises a multiply jointed arm 136 that is connected with the shaft 144 by a clamp 138. A screw 140 allows a separable connection between the bracket 134 and endoscope 110, where the latter can be displaced upward.

As can be seen from the depiction in FIG. 15, two light beams 123, 126 are radiated from the illuminating units 118, 120 and are directed in such a way that they intersect. This allows illumination of both a relatively remotely situated object field 130 and a relatively closely situated object field 128 in optimal manner, that is homogeneously. The depiction in FIG. 15 is not true to scale; the maximum distances between the illuminating units 118 and 120 and the corresponding object field can lie in the range of 1 m. This arrangement with the zero degree lens and the corresponding illuminating direction is selected when sufficient space is available extending over the particular object field.

Figure 16:
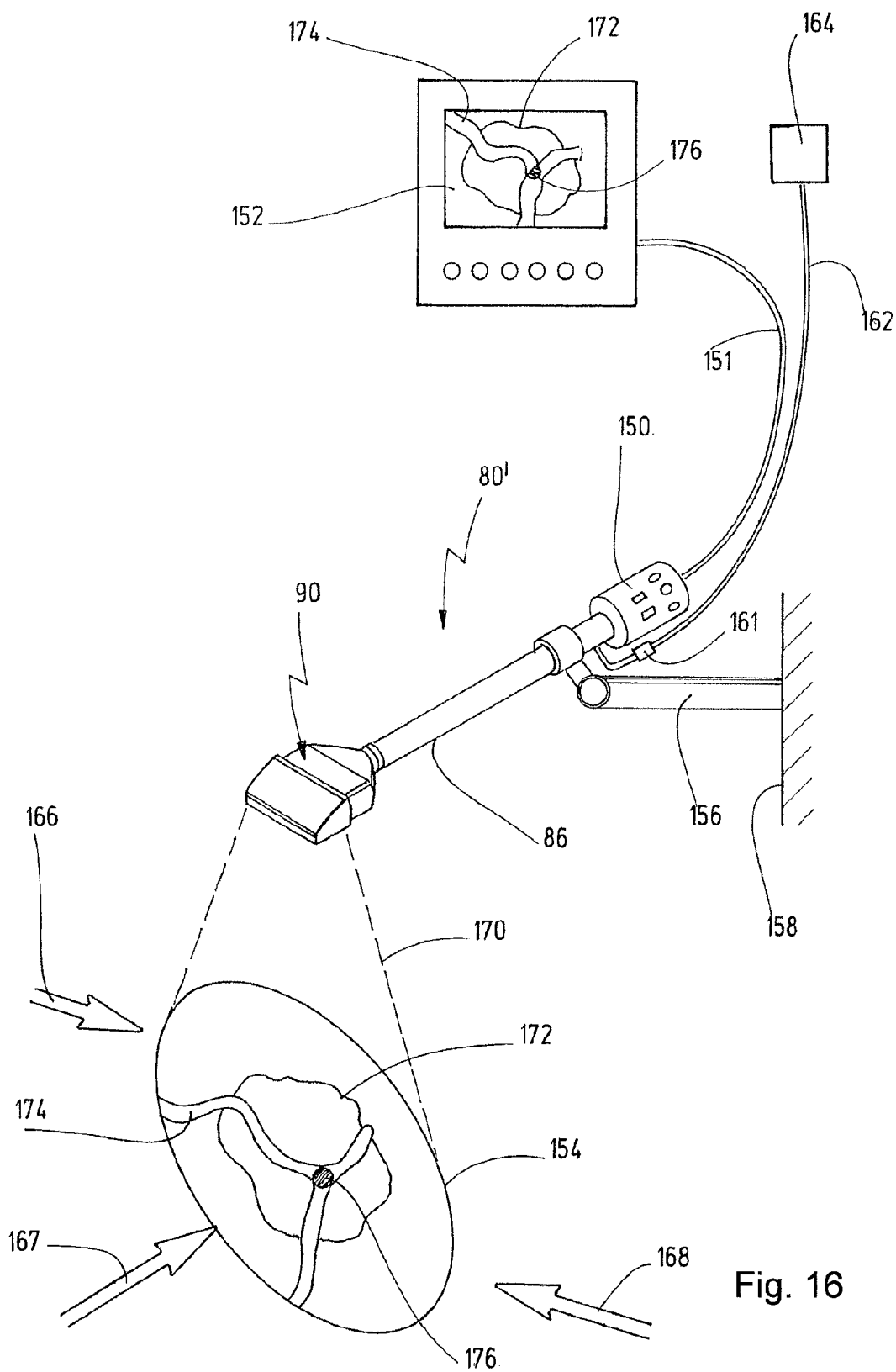
FIG. 16 shows a strongly schematized view of a fourth embodiment of an inventive exoscope with 90 degree view, similar to the configuration of the second embodiment but coupled with a video camera that transmits an image onto a monitor.

In the fourth embodiment shown, in FIG. 16, an exoscope 80' is employed that, where the configuration of the shaft, illumination supply, and the diversion is concerned, is of the same configuration as the embodiment of an exoscope 80 shown in FIGS. 9 through 12. Contrary to this second embodiment, there is a video camera 150 coupled on the eyepiece and connected by a cable 151 with a monitor 152. The exoscope 80' is connected by a bracket 156 to a wall 158. A light conductor connection 161 extending in the proximal direction is connected with a power line 162 that leads to a light source 164 set off to the side. Here too the illuminating units are arranged in such a way that a light beam 170 results that optimally illuminates an object field 154. Located in the illustrated embodiment in an object field 154 is an organ, for example a beating heart, on whose outer arteries 174 a surgical procedure is to be performed in the area of a branching 176. Arrows 166, 167, 168 indicate that the object field 154 is accessible without obstacle to a surgeon or support staff. For all these persons there is the possibility of observing the object field 154 visualized on the monitor 152.

At the beginning of the operation, if the sternum is first to be opened and the organ 172 to be accordingly exposed, then the bracket 156 can hold the exoscope 80' positioned in such a way that the entire sternum area is illuminated over its surface. If then, for example at the branching 176, a procedure is to be performed, then either a corresponding focusing can be accomplished on this site by the video camera 150 or the exoscope 80' or its head member 90 can be moved closer to the object field 154 by the bracket 156. In all positions an optimal illumination and an optimal visual monitoring of the surgical process are possible.

Illustrated in FIGS. 17 and 18 is a fifth embodiment of an inventive exoscope, which is designated in its entirety with reference number 180.

Here again the exoscope 180 comprises a base member 184 in which a lens 182 is enclosed. An eyepiece 183 is present at the proximal end.

The viewing direction 185 of the lens 182 runs at a 90 degree angle to its longitudinal axis.

The lens 182 is contained in a shaft 186 of the exoscope 180. A head member 190 is provided on the distal end 188 of the shaft 186.

As can be recognized in particular from the section view in FIG. 18, the distal end of the lens 182 ends in this head member 190.

A single illumination unit 192 is contained in the head member 190.

Its radiating direction 193 likewise runs at an angle of approximately 90 degrees to the longitudinal axis 187 of the shaft 186, and this longitudinal axis 187 also extends in the direction of the longitudinal axis of the lens 182.

Contained in the shaft 186 are light conductors 194 that comprise a curvature 195 in the head member 190 so that they radiate illuminating light in the radiating direction 193.

On the proximal side the base member 184 comprises a housing 198, from which a light conductor connection 196 protrudes laterally. This light conductor connection 196 is connected by a cable 200 with a light source.

Here too a focusing device 202 is present inside the head member 190.

Said device serves once again not to configure the individual light conductors 194 but rather to guide the illuminating light homogeneously to the surgical site.

It can be recognized from the sectional depiction in FIG. 18 that the image input position of the lens 182 and the light outlet position of the illuminating unit 192 are situated successively in a row in the direction of the longitudinal axis 87 of the exoscope 180.

They can also be situated alongside one another, viewed in the direction of the longitudinal axis 187.

The light beam of the illuminating unit 192 is adjusted by the producer in such a way that at the customary working distances, that is, primarily in the range between 20 and 60 cm, there is homogeneous illumination; that is, the viewing beam of the lens intersects accordingly the illuminating beam of the illuminating light.

A sixth embodiment of an inventive exoscope, shown in FIGS. 19 through 22, is designated in its entirety with reference number 210.

The exoscope 210 comprises a lens 212 that as previously described makes possible a shaft 213 and a window 211 for a 90 degree view from the longitudinal axis of the shaft 213.

The base member of the exoscope 210 consists of a first module 214 and a second module 222.

The first module 214 comprises an elongated shaft 216, which comprises on its proximal end a light conductor connection 218 bent at an angle.

On the distal end the shaft 216 comprises a widened head member 219 in which an illuminating unit 220 is contained.

Here again, as previously described, light conductors 221 in the shaft 216 are conducted to the illuminating unit 220.

The second module 222 likewise comprises a shaft 224, which has on its proximal side an angled light conductor connection 226. Present on the distal end is a widened head member 227 in which an illuminating unit 228 is contained.

Here again light conductors are conducted by the light conductor connection 226 through the shaft 224 to the illuminating unit 228.

Figure 20:
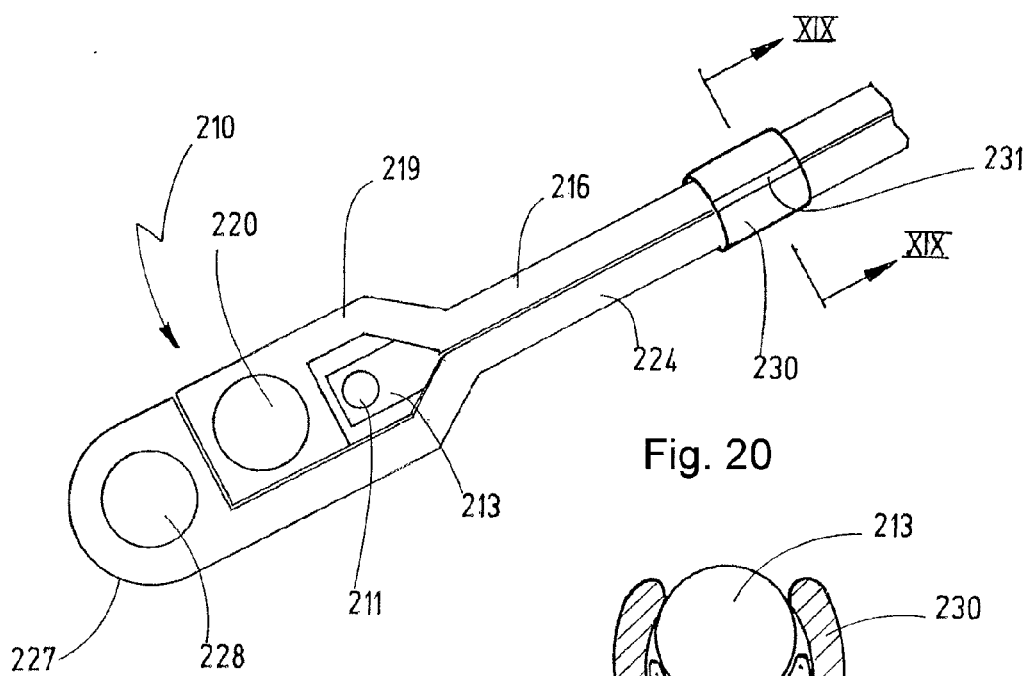
FIG. 20 shows the distal end area of the exoscope of FIG. 19 in assembled state.

FIG. 20 shows how the three component elements, namely the lens 212, the first module 214, and a second module 222, are combined to form the exoscope 210 as an end product.

Figure 19:
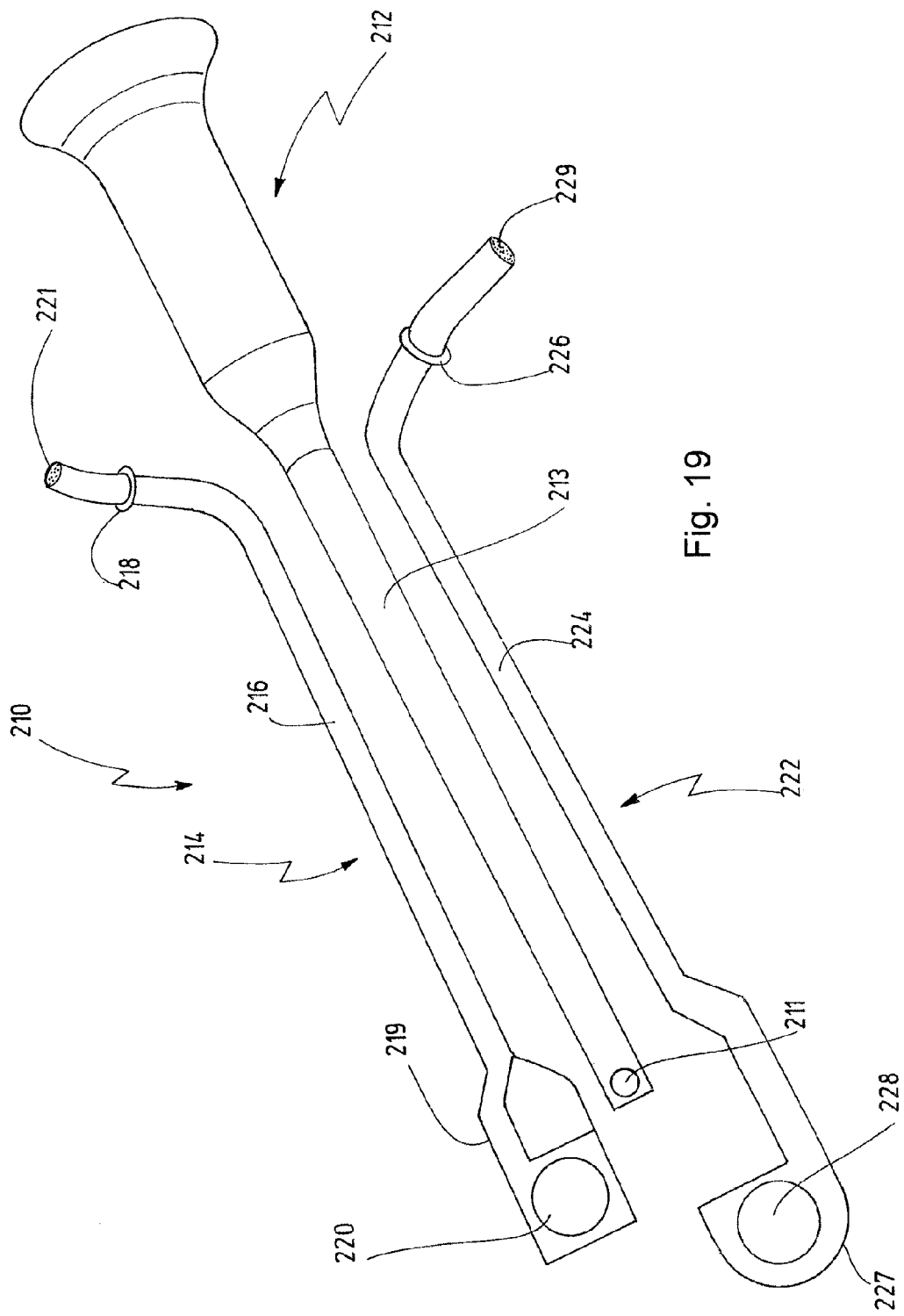
FIG. 19 shows an exploded view of a sixth embodiment of an exoscope in modular structure.

It can be seen in connection with FIG. 19 that the configuration of the head members 219, of the first module 214, and of the head member 227 of the second module 222 are configured in such a way that they can be fused with one another and thereby consequently the two illuminating units 220 and 228 are positioned in a row one after the other, viewed in the longitudinal axis of the shafts 216 and 224.

For this purpose there is present in the head member 227 a corresponding recess, not presented in further detail here, into which the head member 219 can be fittingly inserted laterally, corresponding to the transition from FIG. 19 to FIG. 20.

Figure 21:
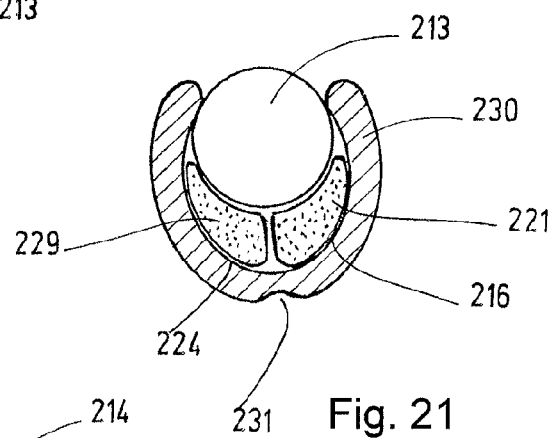
FIG. 21 shows a section along the line XIX-XIX in FIG. 20.

It can be recognized from the sectional depiction in FIG. 21 that the shaft 213 of the lens 212, the shaft 216 of the first module 214, and the shaft 224 of the second module 222 are shaped in such a way that the two shafts 224 and 216 can be closely fitted together on an outer side of the shaft 213.

The combined structure of the three shafts 213, 216, and 224 is held together by a fastening that encloses them in the shape of a clamp.

The clamp 230 comprises a narrowing 231 for better spreading on the outside.

It can be recognized from FIG. 20 that the distal end of the shaft 213 of the lens 212 comes to rest in a vacant area in the head member 219, in such a way that the window 211 in a row and comes to rest, viewed from the proximal toward the distal side, before the row of illuminating units 220, 228.

In practical application, the exoscope 210 can be used, completely assembled, in the condition shown in FIG. 20.

Figure 22:
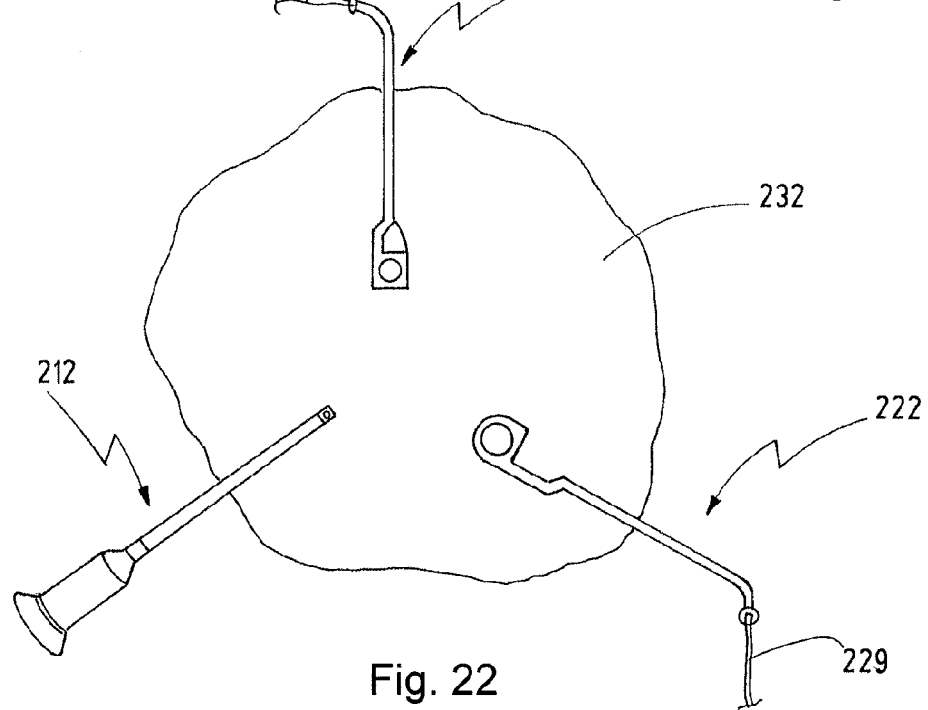
FIG. 22 shows a possible application of the module components in a surgical area.

It is also possible, as shown in FIG. 22, to use the exoscope 210 with components separated from one another.

FIG. 22 indicates a surgical area that is to be observed and illuminated by the exoscope 210.

FIG. 22 indicates that the three components, namely the lens 212, the first module 214, and the second module 222, are positioned approximately in star form, each displaced by 120 degrees, around the surgical area 232. Because both the first module 214 and the second module 222 are provided with their own light conductors 221, 229, and the latter are also conducted to a corresponding illuminating source, the two modules 214 and 222 can be used completely independently of one another but they can also both be employed contiguous with one another.

The star-shaped arrangement is of course only an example; these individual instruments can also be grouped or positioned in distribution at different angles to one another.

The intention here is merely to demonstrate the flexibility that exists for the person conducting the operation to achieve optimal observation and equally favorable illumination in a particular surgical area 232.

The embodiment indicates that each of the modules 214, 222 comprises only one illuminating unit.

It is also possible to construct embodiments in which two or more illuminating units exist. This modular structure not only expands the range of applications but also allows a simple cleaning and sterilization after a use. By releasing the clamp 230, the individual component elements, namely the lens 212, first module 214, and second module 222, can then be separately cleaned, sterilized, and further treated in preparation for another use.

Figure 23:
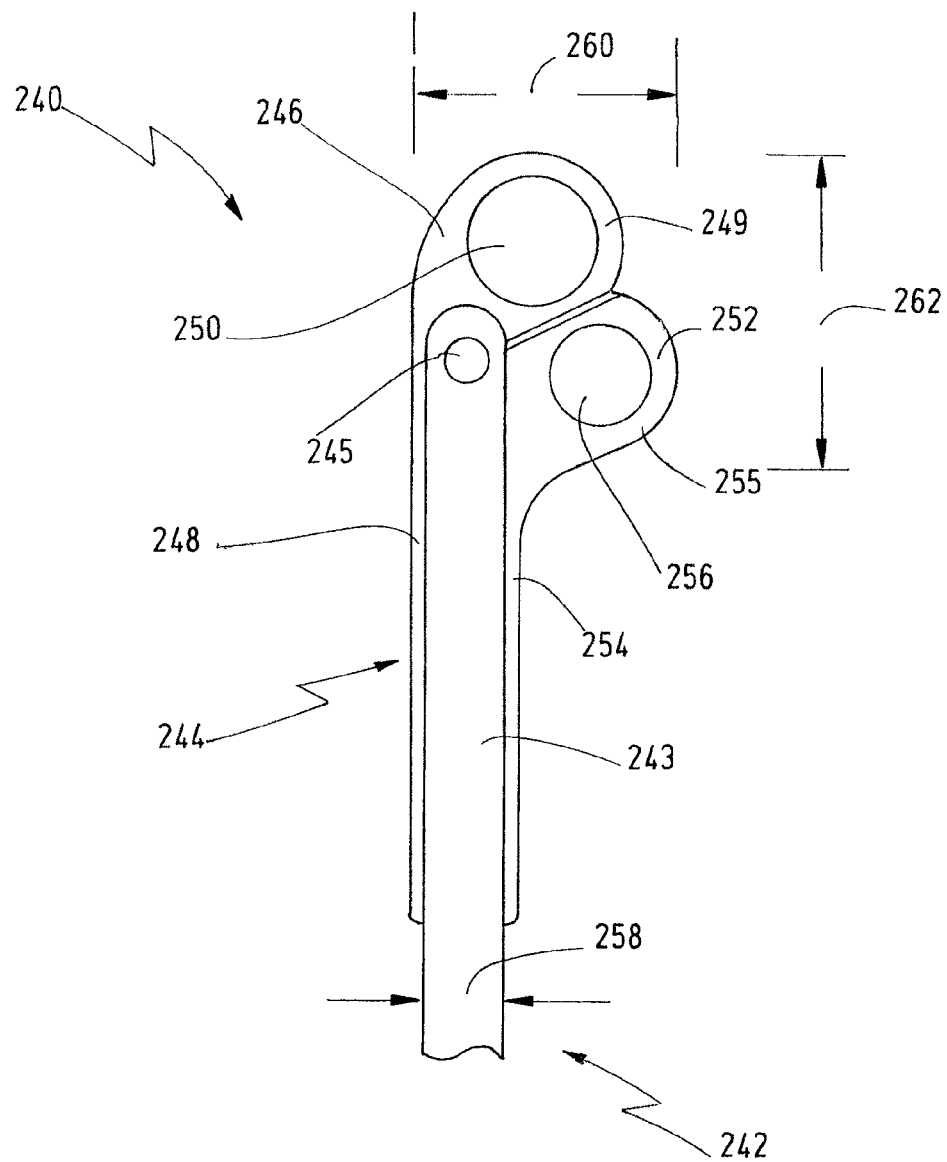
FIG. 23 shows a seventh embodiment of an exoscope with laterally displaced illumination units.

FIG. 23 shows a seventh embodiment of an inventive exoscope, which is designated in its entirety with reference number 240.

The exoscope 240 is also of modular construction.

The exoscope 240 comprises a lens 242, which has an elongated shaft 243 as has been repeatedly described heretofore.

Here too a window 245 is present that allows a 90 degree view from the longitudinal axis of the shaft 243 outward.

The lens 242 is mounted on a base member 244, which itself in turn consists of a first module 246 and a second module 252.

The first module 246 here comprises once again a shaft 248, which comprises a head member 249 positioned laterally with respect to its longitudinal axis, with an illuminating unit 250.

The second module 252 likewise comprises an elongated shaft 254 and is continued likewise in a head member 255 pointing laterally in the same direction as the head member 249, which includes an illuminating unit 256.

The two head members 249 and 255 are contiguous with one another via a straight shared surface. Here too, light conductors, not shown in greater detail, are conducted inside the shafts 248 and 254 to the illuminating units 250 and 256.

This combined structure of a lens 242, first module 246, and second module 252 can be held together, as previously described, by a fastening unit such as a clamp. In this embodiment it is also possible to clip the two modules 246 and 252 to one another or to fasten them together. Thus it is possible to handle the two modules as a base member 244. The lens 242 can be removed from the base member 244 and inserted at another favorable position in the surgical area.

A particular advantage of this configuration with illuminating units 250 and 256 pointed laterally outwards in the same direction from the longitudinal axis of the shafts, is that it becomes possible to work unhindered with tools on the opposite side, that is, on the left side in the depiction in FIG. 23.

A diameter 258 of the shaft 243 of the lens 242 measures approximately 7.5 mm.

The width 260 of the assembled head members 249 and 255 measures about 20 mm. The height 262 of the assembled head members 249 and 255 measures about 25 mm.

It can be seen from this that a markedly widened head member is present in comparison with the shaft or shafts. Nevertheless there is a relatively small, compact configuration of the exoscope 240 in the distal end area.

The structure as shown in FIG. 23 can be arranged horizontally in a lateral configuration to the surgical field; it can be used as such a compact combined structure 240, as a composite of the two module parts 246 and 252 with separate lens 242, or as described before in connection with the exoscope 210, also in the form of three individual components, namely lens 242, first module 246, and second module 252.

Although the invention has been described with reference to a particular arrangement of parts, features and the like, these are not intended to exhaust all possible arrangements or features, and indeed many other modifications and variations will be ascertainable to those of skill in the art.

What is claimed is:

1. An exoscope for observing and illuminating an object field on a patient from a site removed from a body of said patient, comprising
    a shaft;
    a lens system for observing an object field, wherein said lens system is a rod lens system;
    an illumination for illuminating said object field, and
    a bracket for holding said exoscope and for modifying a distance between said lens system and said object field, wherein
    a head member being positioned at a distal end of said shaft;
    said head member being widened in comparison to a diameter of said shaft;
    said illumination reaching into said widened head member, and having at least two radiating illumination units being housed in said widened head member, the at least two radiating illumination units are separate units arranged at a distance one to another, and wherein each of that at least two radiating illumination units is provided with a focusing device having a condenser lens;
    a radiant characteristic of said at least two radiating illumination units being selectable in that, with all possible distances between said object field and said lens system, said object field being homogenously illuminated by said at least two radiating illumination units, and wherein light beams emitted by said at least two radiating illumination units overlap in that at least said object field can be illuminated homogeneously by areas of overlapping light beams, and
    power lines for supplying said at least two radiating illumination units being arranged within said shaft.

2. The exoscope of claim 1, wherein each of said at least one radiating illumination unit comprises distal ends of light conductors guided from a proximal-side light conductor connection via the shaft into said widened head member.

3. The exoscope of claim 2, wherein said light conductors being guided in said shaft as a skein, and wherein in said widened head member, said light conductors have branches leading to each of said at least one radiating illumination unit.

4. The exoscope of claim 1, wherein a viewing direction of said lens system and a radiating direction of said at least one radiating illumination unit occur in a direction of a longitudinal axis of said shaft.

5. The exoscope of claim 1, wherein a viewing direction of said lens system and a radiating direction of said at least one radiating illumination unit occur at an angle from a longitudinal axis of said shaft.

6. The exoscope of claim 5, wherein said angle is up to approximately 90 degrees.

7. The exoscope of claim 5, wherein a diversion of said radiating direction occurs through at least one prism contained in said widened head member.

8. The exoscope of claim 5, wherein a diversion of said radiating direction occurs through at least one mirror contained in said widened head member.

9. The exoscope of claim 5, wherein a diversion of said radiating direction occurs by curved distal ends of flexible light conductors housed in said head member.

10. The exoscope of claim 1, wherein said head member comprises a base member.

11. The exoscope of claim 10, wherein said lens system being configured as a separate component being insertable into said base member.

12. The exoscope of claim 10, wherein a guide device being provided at said shaft for guiding said lens system to said head member when inserting it into said base member.

13. The exoscope of claim 10, wherein said base member can be coupled to said lens system.

14. The exoscope of claim 13, wherein said base member is composed of several modules each of said modules comprising at least one radiating illumination unit together with its respective supply lines.

15. The exoscope of claim 14, wherein each of said modules has a shaft and a head member that can be linked together by a releasable fastening.

16. The exoscope of claim 1, wherein said head member being configured as a closed housing having a proximal site connected to said shaft.

17. The exoscope of claim 1, wherein said lens system comprises a video camera coupled to said lens system and to a monitor for visualizing images from said video camera.

18. The exoscope of claim 17, wherein said lens system comprises an eyepiece enlargement, through which a full-surface image can be achieved on said monitor at all possible zoom settings of said video camera.

19. An exoscope for observing and illuminating an object field on a patient from a site removed from a body of said patient, comprising
    a shaft;
    a lens system for observing an object field;
    an illumination for illuminating said object field, and
    a bracket for holding said exoscope and for modifying a distance between said lens system and said object field, wherein
    a head member being positioned at a distal end of said shaft and comprising a base member that can be coupled to said lens system;
    said base member is composed of several modules each of the modules comprising at least one radiating illumination unit together with its respective supply lines and each of the modules has a shaft and a head member that can be linked together by a releasable fastening;
    said head member being widened in comparison to a diameter of said shaft;
    said illumination reaching into said widened head member, and having at least one radiating illumination unit being housed in said widened head member, a radiant characteristic of said at least one radiating illumination unit being selectable in that, with all possible distances between said object field and said lens system, said object field being homogenously illuminated by said at least one radiating illumination unit, and
    power lines for supplying said at least one radiating illumination unit being arranged within said shaft.

* * * * *